United States Patent
Brennan et al.

(10) Patent No.: US 6,508,781 B1
(45) Date of Patent: Jan. 21, 2003

(54) ULTRASONIC ABLATION CATHETER TRANSMISSION WIRE CONNECTOR ASSEMBLY

(75) Inventors: Lawrence Brennan, Temecula, CA (US); Wayne E. Cornish, Fallbrook, CA (US); Douglas H. Gesswein, Temecula, CA (US); Martinos Tran, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/476,749

(22) Filed: Dec. 30, 1999

(51) Int. Cl.$^7$ ............................................. A61B 17/20
(52) U.S. Cl. ........................................ 604/22; 600/467
(58) Field of Search ............................. 604/22, 95.04, 604/19, 27, 28, 48, 93.01, 164.01, 164.02, 164.13, 171, 173, 264, 284, 523, 528, 533, 534, 536, 905; 606/128; 600/437, 439, 459, 462, 466, 467, 471; 607/115, 116, 120, 121, 122

(56) References Cited

U.S. PATENT DOCUMENTS

| | | |
|---|---|---|
| 4,870,953 A | 10/1989 | DonMicheal et al. ......... 128/24 |
| 5,267,954 A | 12/1993 | Nita .............................. 604/22 |
| 5,312,328 A | 5/1994 | Nita et al. ..................... 604/22 |
| 5,342,292 A | 8/1994 | Nita et al. ..................... 604/22 |
| 5,368,557 A | 11/1994 | Nita et al. ..................... 604/22 |
| 5,382,228 A | 1/1995 | Nita et al. ..................... 604/22 |
| 5,397,301 A | * 3/1995 | Pfleuger et al. |
| 5,427,118 A | 6/1995 | Nita et al. .................. 128/772 |
| 5,540,656 A | * 7/1996 | Pfleuger et al. |
| 5,542,917 A | * 8/1996 | Nita et al. |
| 5,735,811 A | 4/1998 | Brisken ........................ 604/22 |
| 5,846,218 A | 12/1998 | Brisken et al. ............... 604/22 |
| 5,989,208 A | 11/1999 | Nita ............................. 604/22 |
| 6,290,656 B1 | 9/2001 | Boyle et al. ................ 600/585 |

* cited by examiner

Primary Examiner—Brian L. Casler
Assistant Examiner—Mark Han
(74) Attorney, Agent, or Firm—Fulwider Patton Lee & Utecht, LLP (57) ABSTRACT

An ultrasonic angioplasty device includes a catheter and a connector assembly for interconnecting an ultrasound transmission member to an ultrasound transducer. A rotation control device is provided that prevents the ultrasound transmission member from rotating relative to the catheter. Rotation is prevented by a fastener aligning the connector assembly with the elongated catheter body, or a key member that fits in a correspondingly shaped slot in a proximal shaft portion of the catheter, for preventing rotation of the connector assembly relative to the catheter.

12 Claims, 6 Drawing Sheets

ULTRASONIC ABLATION CATHETER TRANSMISSION WIRE CONNECTOR ASSEMBLY

BACKGROUND

The invention relates generally to medical devices, and more particularly to an improved connector assembly for connecting an ultrasound transmission member to an ultrasound transducer for use in an ultrasonic angioplasty catheter.

In typical percutaneous transluminal coronary angioplasty ("PTCA") procedures, a guiding catheter having a preformed distal tip is percutaneously introduced into the cardiovascular system of a patient through the brachial or femoral arteries and advanced therein until the distal tip is in the ostium of the desired coronary artery. A guide wire and a dilatation catheter having a balloon on the distal end are introduced through the guiding catheter with the guide wire slidably disposed within an inner lumen of the dilatation catheter. The guide wire is first advanced into the patient's coronary vasculature until its distal end crosses the lesion to be dilated and then the dilatation catheter is advanced over the previously introduced guide wire until the dilatation balloon is properly positioned across the lesion. The balloon may then be inflated to treat the lesion. Thereafter, a stent device may be located at the treated lesion, if deemed necessary.

In "ultrasonic" angioplasty, an ultrasonic angioplasty catheter is similarly advanced to an area of vascular blockage, and mechanical vibration at ultrasonic frequencies, generated typically by a piezoceramic transducer, is delivered along an elongated ultrasonic angioplasty transmission member or wire to a distal catheter tip. When the distal catheter tip is abutted against intravascular blockage, the vibration of the distal end of the ultrasonic angioplasty transmission member removes the obstruction by mechanical impact and cavitation.

Ultrasonic angioplasty transmission members are commonly connected to an extra-corporeal source of ultrasonic energy, so that it is generally necessary to deliver the ultrasonic energy over a relatively long distance, such as approximately 150 cm., to the intravascular blockage to be treated. Over such a distance, the ultrasonic energy attenuates as it passes along the length of the ultrasonic angioplasty transmission member, resulting in a loss of system efficiency, and requiring the delivery of a greater amount of acoustic energy to the ultrasonic angioplasty transmission member than actually reaches the treatment site, which can increase fatigue of the ultrasonic angioplasty transmission member and thereby increase the chances of fracturing and breakage during use, especially when the wires are bent. It is therefore desirable to provide an ultrasonic angioplasty transmission member mounting that has a lower loss of the ultrasonic energy so that lower levels of energy may be applied to the member.

Amplification of the ultrasonic vibrations typically occurs at areas of reduced cross-sectional diameter. Regions where the highest amplification occurs are generally located where the transition to a reduced diameter occurs, at the proximal end of a smaller diameter section where transverse vibration of ultrasonic energy transmitted from a larger section is amplified. These areas are prone to higher stresses due to increased longitudinal and transverse vibration as a result of amplification. One such area is a connection point of the ultrasound transmission member to the ultrasonic transducer. There typically exists a significant step down resulting in amplification. Firmly connecting the member to the transducer will result in fewer inefficiencies.

Accurate positioning of the ultrasonic angioplasty catheter and ultrasound transmission member in the vascular system to be treated is important for the successful application of ultrasonic energy to an intravascular blockage. It is therefore desirable that the ultrasound transmission wire and ultrasound transducer be firmly aligned with the catheter. It is important that as few losses as possible occur between the application of ultrasonic energy to the ultrasonic wire at its proximal end by the ultrasound transducer and the application of that ultrasonic energy at its distal end to the vascular blockage. The ultrasonic angioplasty transmission member should not rotate independently of the rest of the catheter due to transverse or longitudinal vibrations. Rotation of the wire inside the catheter dampens the transmission of ultrasonic energy through the wire resulting in a less efficient energy transfer. Firmly mounting the wire in place will increase the efficiency in that less energy is absorbed by the wire.

Since the connection point of an ultrasonic transducer to the ultrasound transmission wire is the region where the greatest amplification of ultrasonic energy occurs due to the large reduction in diameter, it is possible for the ultrasonic angioplasty transmission member to rotate independently of the rest of the catheter due to transverse or longitudinal vibrations during use. Such rotation can interfere with the accurate positioning of an ultrasonic angioplasty catheter and the included ultrasound transmission member in the vascular system. While conventional connector assemblies are known that firmly grip and hold the ultrasound transmission member in relation to the ultrasound transducer, they can permit rotation of the ultrasound transmission member and connector assembly relative to the ultrasonic angioplasty catheter during use.

An ultrasound catheter having an ultrasound transmission member or wire and a proximal end member connector assembly is known from U.S. Pat. No. 5,382,228 to Nita et al. The proximal end member connector assembly of U.S. Pat. No. 5,382,228 can include a compressible gripping ferrule, compressible plugs, or a combination of both, for securing the ultrasound transmission member or wire to an ultrasound transducer. The compressible gripping ferrule is received in a proximal connector member threadedly connected to a transducer horn, and has a small aperture through which the ultrasound transmission member passes. A frontal member compresses the gripping ferrule to cause the gripping ferrule to firmly grip and hold the ultrasound transmission member to the transducer. The proximal connector member can then be compressed or crimped inwardly to additionally hold the ultrasound transmission member. Although the '228 patent represents an advance in the art, such a connector assembly can permit rotation of the ultrasound transmission member and connector assembly relative to the ultrasonic angioplasty catheter, particularly under the stress of longitudinal and transverse vibrations during use.

Hence, those skilled in the art have recognized a need for an improved connector assembly to more efficiently transfer ultrasonic energy to an ultrasound transmission member to lessen inefficiencies. Further, those skilled in the art have recognized a need for a mounting system that keeps the connector assembly and the ultrasound transmission member from rotating independently relative to the ultrasonic angioplasty catheter. The present invention fulfills this need and others.

SUMMARY OF THE INVENTION

Briefly, and in general terms, the present invention is directed to an improved connector assembly for connecting an ultrasound transducer and an ultrasound transmission member of an ultrasonic angioplasty catheter. Further it is directed to an improved device to prevent the connector assembly and ultrasound transmission member from rotating independently relative to the ultrasonic angioplasty catheter.

In one aspect, there is provided an ultrasonic angioplasty device for connection to an ultrasound transducer, the ultrasonic angioplasty device comprising an elongated catheter body having a lumen extending longitudinally therethrough, the catheter body having a proximal end and a distal end, an ultrasound transmission member located in the lumen of the catheter body and having a distal end for applying ultrasonic energy to a biological subject, and having a proximal end, a connector assembly configured to connect the proximal end of the ultrasound transmission member to an ultrasound transducer, and a rotation control device comprising a control shaft disposed at the proximal end of the ultrasound transmission member and coupled to the proximal end of the elongated catheter body such that rotation of the control shaft controls rotation of the catheter body, and comprising an interconnection device interconnecting the connector assembly with the control shaft that prevents rotation of the connector assembly and the ultrasound transmission member relative to the control shaft thereby preventing rotation of the ultrasound transmission member relative to the catheter body.

In more detailed aspects, the interconnection device of the rotation control device comprises a fastener for aligning and interconnecting the connector assembly with the control shaft. The connector assembly in another aspect comprises a key member and the control shaft comprises a surface defining a correspondingly shaped slot for receiving the key member for preventing rotation of the connector assembly relative to the control shaft. In yet more detail, the connector assembly comprises a compressible gripping ferrule having a surface defining an aperture through which the ultrasound transmission member passes, a front connector screw member having a surface defining an aperture through which the ultrasound transmission member passes and having an exterior threaded portion, and a crimp screw connector member connectable to the ultrasound transducer, the crimp screw connector member having a surface defining an aperture through which the ultrasound transmission member passes and having a longitudinal bore in which the compressible gripping ferrule is disposed, the longitudinal bore having an internally threaded portion for threadably receiving the exterior threaded portion of the front connector screw member, whereby the front connector screw member compresses the gripping ferrule in the crimp screw connector member, to cause the gripping ferrule to firmly grip and hold the ultrasound transmission member In further aspects, the control shaft includes a surface defining a first transverse bore, the crimp screw connector member has a surface defining a second transverse bore, and the rotation control device comprises a dowel member disposed in the first and second transverse bores to align the control shaft and the crimp screw connector member to prevent the crimp screw connector member and the ultrasound transmission member from rotating relative to the control shaft and thereby preventing the ultrasound transmission member from rotating relative to the elongated catheter body. In another detailed aspect, a key member is disposed on the crimp screw connector member, and wherein the control shaft has a surface defining a correspondingly shaped slot for receiving the key member for preventing rotation of the crimp screw connector member relative to the control shaft.

In yet other aspects, the key member comprises an annular member having a square outer shape. In another aspect, the key member captures the crimp screw connector member, and wherein the key member has a surface defining an aperture for receiving a portion of the crimp screw connector member, and the portion of the crimp screw connector member and the aperture of the key member have corresponding shapes for preventing rotation of the crimp screw connector member relative to the key member. Further, the aperture of the key member has a square shape.

These and other aspects and advantages of the invention will become apparent from the following detailed description and the accompanying drawings, which illustrate by way of example the features of the invention.

DETAILED DESCRIPTION OF THE PREFERRED EMBODIMENTS

Figure 1:
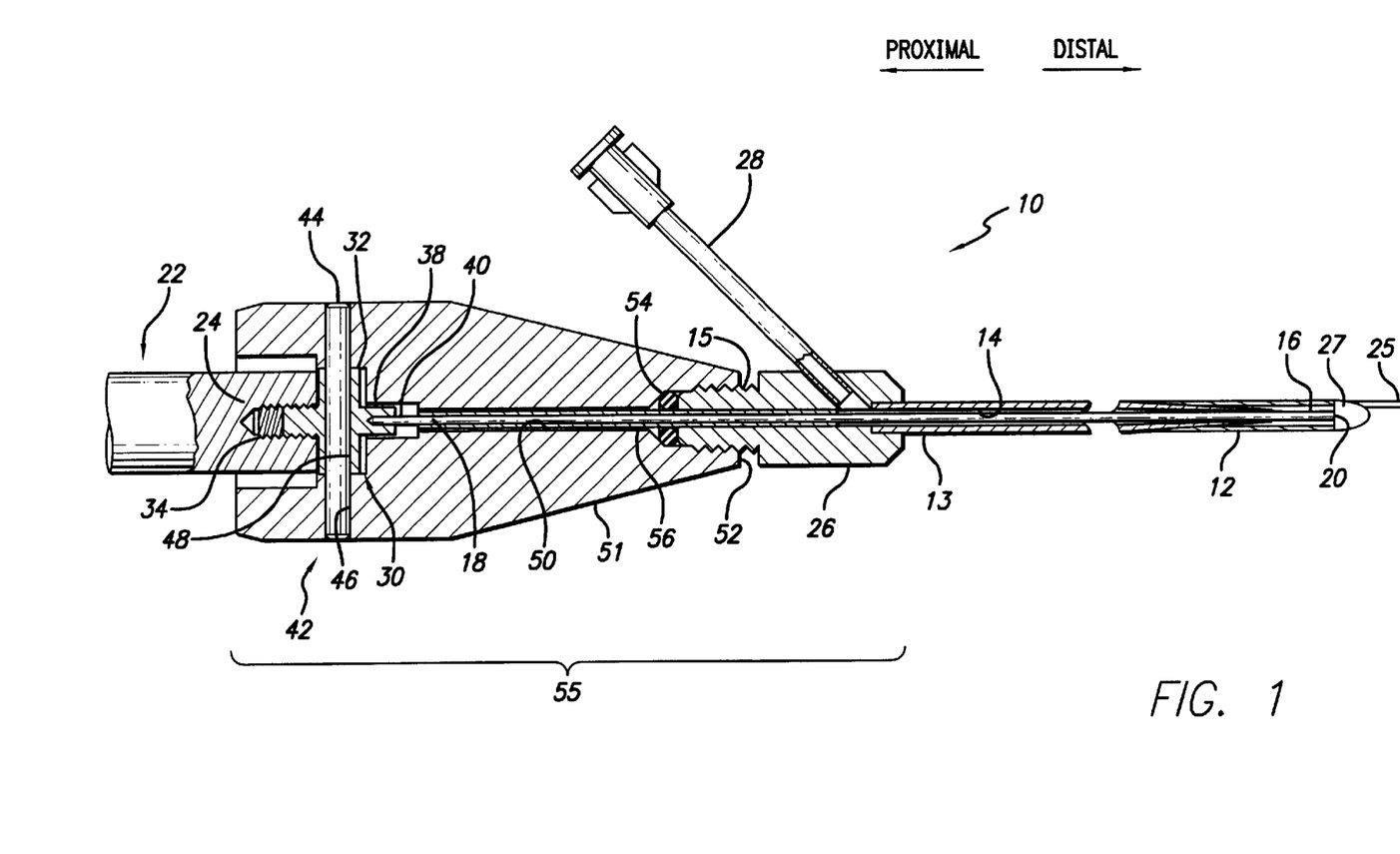
FIG. 1 is a cross-sectional view of the proximal end of an ultrasonic angioplasty device illustrating a first embodiment of a rotation control device including a clamp for preventing a connector assembly and ultrasound transmission member from rotating relative to the elongated catheter body according to principles of the invention.

Referring now to the drawings in which like reference numerals are used to refer to like or corresponding elements among the several views, there is shown in FIG. 1 an ultrasonic angioplasty device 10 including an elongated ultrasonic angioplasty catheter body 12 having an inner lumen 14 extending longitudinally AL through the catheter body. An elongate ultrasound transmission member or wire 16 having a proximal end 18 and a distal end 20 for applying ultrasonic energy to an area of vascular blockage (not shown) extends through the length of the elongated catheter body. The ultrasonic angioplasty device 10 is connected to an ultrasound transducer or horn 22 for generating ultrasonic vibrational energy. The transducer 22 has a distal transducer portion 24 to which the proximal end of the ultrasound transmission member or wire is connected. As is shown in FIG. 1, the ultrasonic angioplasty device may also include a hub 26 having a side arm/infusion port 28 for infusion of fluids, such as medicines or drugs into the vasculature. Although not shown as such, the side arm 28 may also be used for the introduction and control of a guide wire through the catheter body 12.

A guide wire 25 is extending from the distal head 27 of the catheter body 12 through an aperture in the distal head. For reasons of clarity of illustration, the guide wire 25 is not shown in position through the side arm 28 and is also not shown within the catheter body. To accommodate a guide wire 25, the catheter body may include another lumen, as will be discussed below. Further, in this embodiment, the distal head 27 is fixedly attached to the catheter body 12 by adhesive or other means and is also fixedly attached to the ultrasound transmission member 16.

The ultrasonic angioplasty device 10 includes a connector assembly 30 for connecting the proximal end 18 of the ultrasound transmission member 16 to the distal transducer portion 24. In the embodiment shown in FIG. 1, the connector assembly 30 comprises a crimp screw connector 32 having a proximal exterior threaded portion 34 for threaded engagement with the threads of the distal transducer portion 24, and includes at its distal end 38 an aperture 40 into which the ultrasound transmission member 16 extends. The ultrasound transmission member 16 extends into the aperture 40 for a predetermined distance and is then crimped into place to fixedly hold the member 16 to the crimp screw connector 32. Because the screw connector 32 is threadably secured to the distal transducer portion 24 of the ultrasound transducer 22, ultrasonic energy at the transducer 22 is conducted to the ultrasound transmission member 16 and from there through the ultrasound transmission member 16 to the distal head 27 for application to vasculature blockages.

FIG. 1 presents an embodiment of a catheter body mounting. As shown, the catheter body 12 has a proximal portion 13 that terminates within the hub 26. The catheter body is typically affixed to the hub with adhesive. The hub 26 is connected to a control shaft 51 through threads 15. The control shaft is used to manipulate the catheter during a procedure. While the ultrasound transmission wire 16 is crimped into a fixed position in the crimp screw connector 32, the crimp screw connector 32, and therefore the ultrasound transmission wire 16, can rotate within the control shaft 51 as a result of transverse and longitudinal ultrasound vibrations. The ultrasound transmission wire 16 can therefore rotate in relation to the control shaft 51, hub 26, and catheter body 12. As mentioned above, rotation of the ultrasound transmission wire 16 within the catheter body 12 during use may cause it to rotate in relation to the catheter body thus dampening the ultrasonic energy and causing the ultrasound transmission member 16 to be less efficient.

To secure the transmission wire 16 in relation to the catheter body 12, a clamp 42 is applied. In this case, the clamp comprises a dowel member or pin 44 inserted through a pair of aligned bores 46 and 48 formed through the control shaft 51 of the catheter 12 and through the crimp screw connector 32 respectively. The pin 44 has the effect of securing the crimp screw connector 32 in relation to the catheter body 12 so that rotation between the two is not possible. In one presently preferred embodiment, the fastener can be a dowel member or pin that fits snugly in the bores of the control shaft 51 and the crimp screw connector 32, although other fasteners, such as a cotter pin or bolt, may also be suitable.

In the embodiment of FIG. 1, the control shaft 51 includes a distal threaded aperture 52 sealed with an O-ring 54 for receiving a male threaded connector portion of the infusion port hub 26. The hub 26 in the case of FIG. 1 includes only a single side arm with an infusion port 28 and is screwed into an opening of the control shaft. However, the port may also be used for a guide wire, and a different hub may be used having multiple side arms and ports. The control shaft also includes a lumen 50 for receiving the ultrasound transmission member 16. Within the lumen 50 of the control shaft and at least a portion of a lumen in the hub, the ultrasound transmission wire 16 is covered with a low friction sleeve 56, such as Teflon™, to permit free movement of the ultrasound transmission member 16. Compression of the O-ring 54 around the ultrasound transmission member 16 and the sleeve 56 prevent the flow of fluids to the crimp screw connector 32, which may have the detrimental effect of dampening vibrations.

The foregoing has presented details of an embodiment of a rotation control device 55 that functions to prevent the ultrasound transmission member 16 from rotating relative to the catheter body 12. The rotation control device comprises the control shaft 51 which is rigidly coupled to the catheter body 12, and an interconnection device between the control shaft and the connector assembly 30, which is rigidly connected to the ultrasound transmission member 16. In this embodiment, the interconnection device comprises the clamp 42 that interconnects the control shaft and the connector assembly. In this embodiment, the control shaft 51 is coupled to the catheter body 12 through a hub 26, although in other embodiment, no hub, or a greater number of hubs may be present. In these embodiments, the control shaft will be rigidly connected to the catheter body 12 such that rotation of the catheter body 12 about its longitudinal axis is controlled by rotation of the control shaft 51. Although the proximal end 13 of the catheter body 12 ends in the hub in FIG. 1, the proximal end 13 may end in the control shaft 51 in the case where no hub is used.

As is discussed above, the connector assembly 30 includes a means for rigidly attaching the ultrasound transmission member 16 to the connector assembly so that rotational motion of the connector assembly about its longitudinal axis controls rotation of the ultrasound transmission member about its longitudinal axis. In the embodiment of FIG. 1, this means comprises the crimp screw connector 32 where the proximal end of the ultrasound transmission member is placed into the distal aperture 40 of the crimp screw connector 32 and is then crimped into place.

Figure 2:
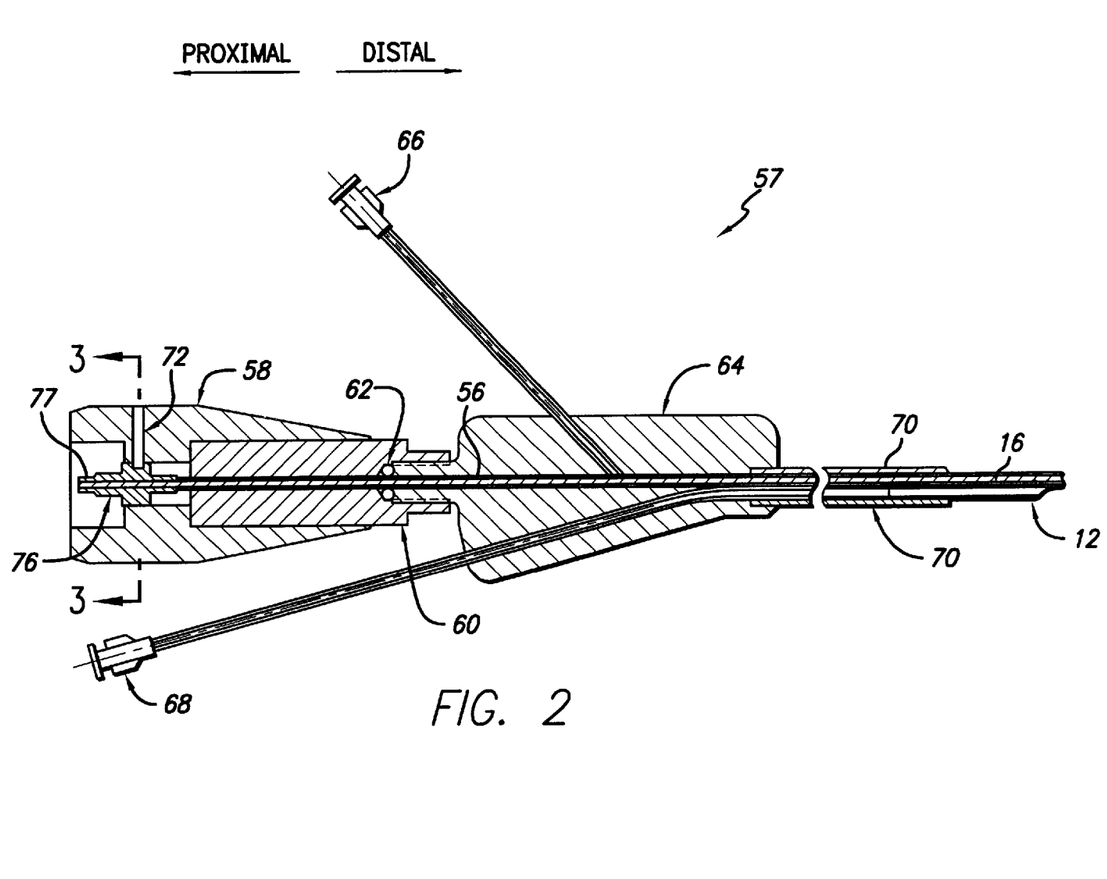
FIG. 2 presents an alternate embodiment of a clamp and connector assembly for preventing the connector assembly and ultrasound transmission member from rotating relative to the elongated catheter body.

Other techniques for securing the ultrasound transmission member 16 so that it does not rotate in relation to the catheter body 12 are possible and another technique is shown in the embodiment of FIG. 2. In this embodiment, the control shaft 58 includes a compression nut 60 that compresses the O-ring 62 against the male connector extension member of a hub 64 to prevent fluid flow to the ultrasonic transducer (not shown in this figure). The male connector extension of the hub 64 includes threads for connection to the compression nut 60.

The compression nut 60 is held in the control shaft by adhesive. In the embodiment shown in FIG. 2, the hub 64 includes two side arms usable as not only an infusion port 66 but also a guide wire port 68. The hub includes a strain relief 70 over a portion of the catheter body 12. The strain relief and the catheter body both terminate in the hub and are held in position by adhesive or other means.

It should be noted that in both FIGS. 1 and 2, the hub is shown with a male connector and the control shaft includes a complementary female connector. In other embodiments, the connector types may be reversed wherein the hub has a female connector and the control shaft a male connector, or other types of connectors may be used.

Figure 3:
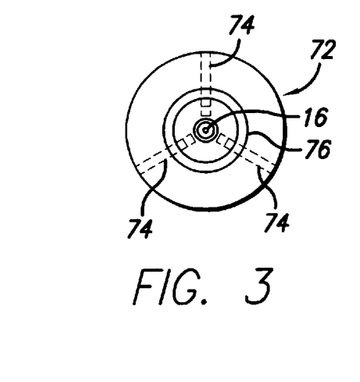
FIG. 3 is a view taken along lines 3—3 of FIG. 2 showing an end and cross-sectional view of the clamp of FIG. 2 in greater detail.

An alternate clamp 72 is shown in the embodiment of FIGS. 2 and 3. FIG. 2 is a cross-sectional view of an ultrasonic angioplasty device 57 and FIG. 3 is a cross-sectional view of a part of the control shaft 58 of FIG. 2. In the ultrasonic angioplasty device 57 shown in FIG. 2, a set of three dowels 74 are positioned through the control shaft 58 and into a crimp screw connector member 76 thereby interconnecting the control shaft 58 and the connector member 76. In this embodiment, the dowels 74 are disposed at angles of 120° from each other, as is more clearly shown in FIG. 3. The dowels 74 do not extend completely through the crimp screw connector member 76 because the ultrasonic transducer 16 is positioned axially through the crimp screw connector member. The crimp screw connector member 76 holds the ultrasound transmission member 16 in a fixed relationship such that neither rotate in relation to each other.

The ultrasound transmission member 16 is positioned in the crimp screw connector member 76 as shown in FIG. 2 and extends to the most proximal point of the crimp screw connector member. The proximal end 77 of the crimp screw connector member is then crimped down onto the ultrasound transmission member 16 to fix it into place. Crimping is done with a crimp die that is activated by manual, electrical, or pneumatic pressure. In one embodiment, the proximal end 77 of the crimp screw connector member is crimped into a hexagonal shape by the crimping tool.

In addition, the multiple dowels 74 clamp the control shaft 58 to the crimp screw connector member 76 and therefore also to the ultrasound transmission member 16. The rigid coupling of the catheter body 12 to the control shaft through the hub 64 and the compression nut 60, and the rigid coupling of the control shaft to the ultrasound transmission member 16 by means of the dowels has the effect of preventing the ultrasound transmission member 16 from rotating in relation to the catheter body 12.

Figure 4:
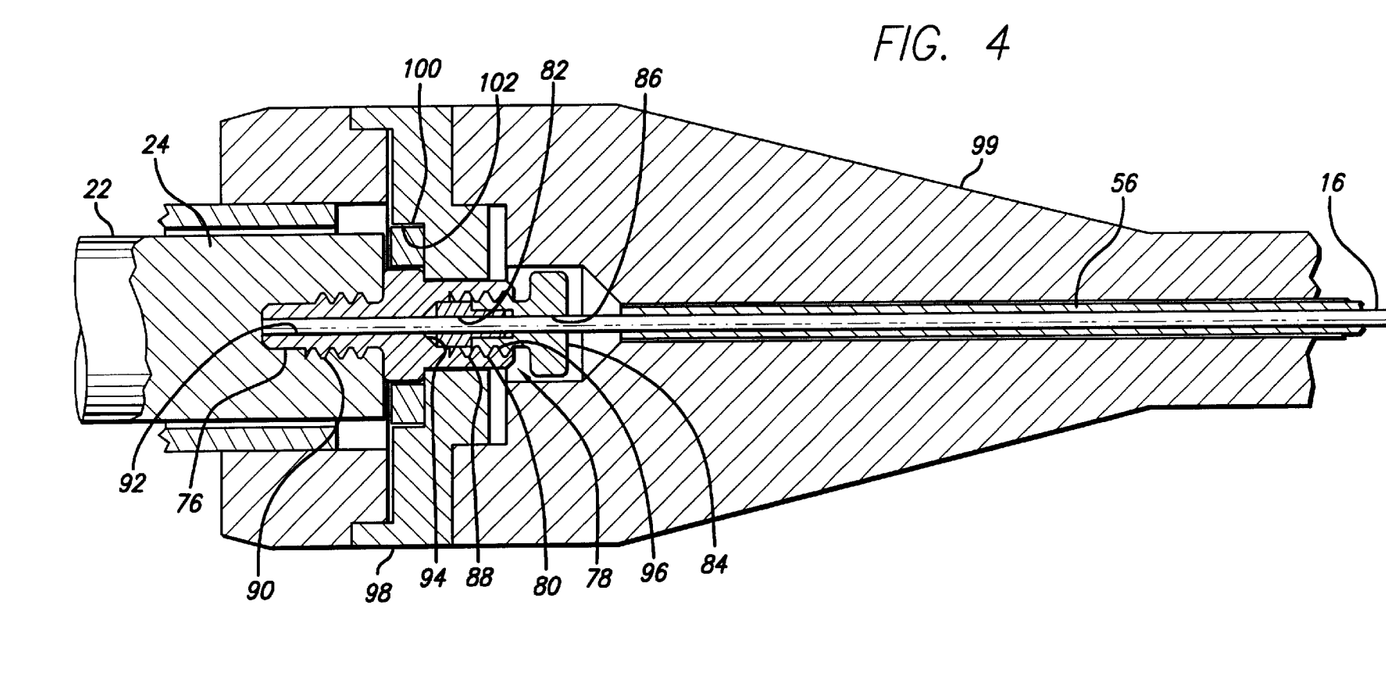
FIG. 4 is an enlarged cross-sectional view of the connector assembly of FIG. 2 with an alternate clamp for preventing the connector assembly and ultrasound transmission member from rotating relative to the elongated catheter body.

Referring now to FIG. 4, the crimp screw connector member 76 and its operation in a connector assembly 78 for connecting the proximal end of the ultrasound transmission member 16 to the ultrasonic transducer 22 are shown. In the embodiment shown, the connector assembly 78 comprises a compressible gripping ferrule 80 having an aperture 82 through which the ultrasound transmission member 16 extends. A front connector screw member 84 has an aperture 86 through which the ultrasound transmission member 16 extends, and has an exterior threaded portion 88 for threaded engagement with the crimp screw connector member 76. The crimp screw connector member 76 also has a proximal exterior threaded portion 90 for threaded engagement with the distal transducer portion 24, and includes an aperture 92 through which the ultrasound transmission member 16 extends. The crimp screw connector member 76 includes a longitudinal bore 94 for receiving the compressible gripping ferrule 80, and the longitudinal bore 94 further includes an internally threaded portion 96 for threadably receiving the exterior threaded portion of the front connector screw member, whereby the front connector screw member 84 compresses the gripping ferrule 80 in the crimp screw connector member 76 to cause the gripping ferrule 80 to firmly grip and hold the ultrasound transmission member 16.

With continued reference to FIG. 4, an alternate embodiment of a clamp 98 is shown that prevents the connector assembly 78 and the ultrasound transmission member 16 from rotating independently relative to the control shaft 99 and therefore also relative to the elongated catheter body 12 (not shown). The clamp 98 comprises a key member 100 disposed on the crimp screw connector member 76, and the control shaft 99 has a surface defining a correspondingly shaped slot 102 for receiving the key member 100, for preventing rotation of the crimp screw connector member 76 relative to the control shaft 99. In one currently preferred embodiment, the key member 100 comprises an annular member having a substantially square outer shape and a central aperture with a substantially square shape, although other outer geometries of the key member such as are typical of nuts, such as hexagonal shape, for example, would also be suitable as long as clamp of the proximal shaft portion of the elongated catheter body has a correspondingly shaped slot 102, allowing the control shaft 99 to capture the key member. The key member 100 thus interconnects the control shaft 99 with the connector member 76.

Figure 5:
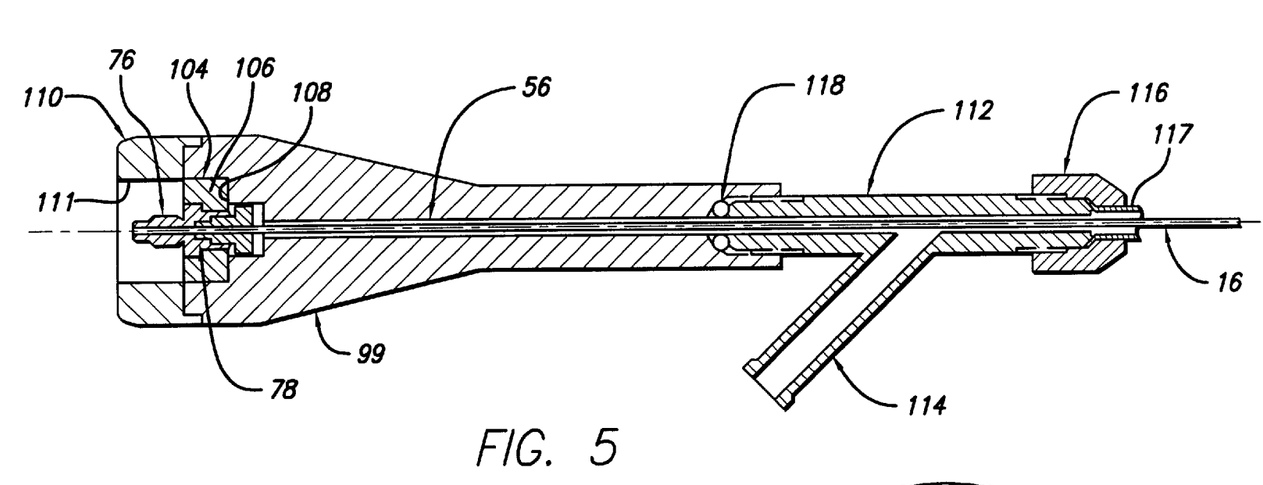
FIG. 5 shows the connector assembly of FIG. 4 with an alternate embodiment of a clamp for preventing the connector assembly and ultrasound transmission member from rotating relative to the elongated catheter body.
Figure 6:
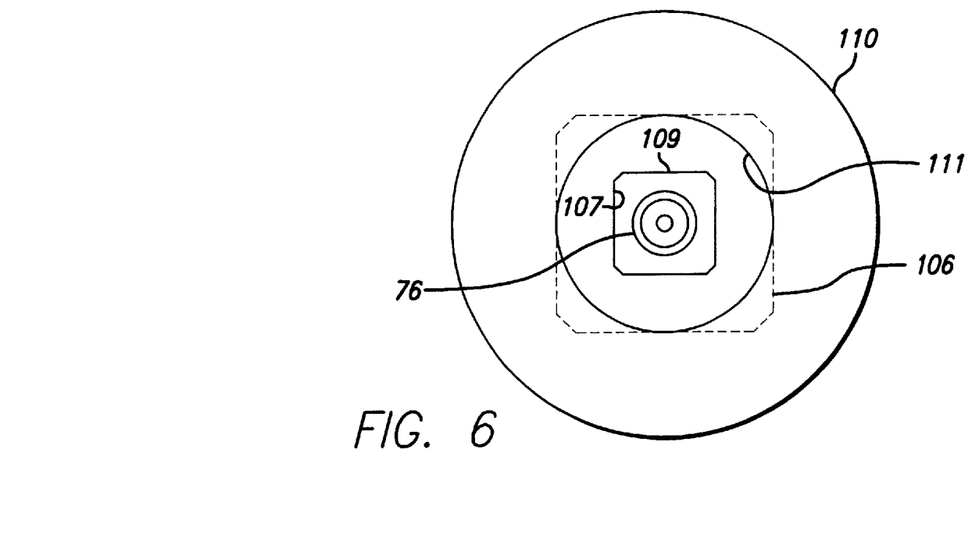
FIG. 6 is an end view of the connector assembly of FIG. 5 showing the configuration of the crimp screw connector and clamp.

Referring now to FIGS. 5 and 6, yet another clamp 104 is shown. As is illustrated in FIG. 5, the connector assembly 78 is the same as that shown in FIG. 4 and comprises the crimp screw connector member, the ferrule, and the front connector screw member. However the clamp 104 for preventing rotation of the ultrasound transmission member 14 in relation to the control shaft 99 is different. In this embodiment, the clamp 104 is of the "nest" variety that captures the crimp screw connector member 76 to prevent the crimp screw connector member from rotating relative to the catheter shaft, particularly as the crimp screw connector member and the ultrasound transducer horn portion are screwed together. The clamp 104 comprises a key member 106 disposed on the crimp screw connector member 76, and the control shaft 99 has a surface defining a correspondingly shaped slot 108 for receiving the key member 106, for preventing rotation of the crimp screw connector member 76 relative to the control shaft 99. Once again, a key member performs an interconnection function between the control shaft 99 and the connector member 76.

As is illustrated in FIG. 6, in one currently preferred embodiment, the key member 106 comprises an annular member having a substantially square outer shape and a central aperture 107 also having a substantially square shape, although other geometries of the key member and its central aperture such as are typical of nuts, such as a hexagonal shape for example, would also be suitable as long as the proximal shaft portion of the elongated catheter body has a correspondingly shaped slot 108, allowing the catheter body to capture the key member. The crimp screw connector member 76 similarly has a shoulder portion 109 with an outer shape corresponding to the inner shape of the central aperture of the key member, allowing the key member to capture the crimp screw connector member. The crimp screw connector member 76 of FIG. 4 similarly has a shoulder portion with an outer shape corresponding to the inner shape of the central aperture of the key member of FIG. 4. The outer ring 110 is preferably mounted to the catheter shaft, and operates to support the connection of the ultrasound transducer horn portion and the catheter shaft by providing a recessed aperture 111 to receive the ultrasound transducer horn portion.

Also shown in the embodiment of FIG. 5 is a hub or Y-connector 112 that includes an infusion port 114 and a compression nut 116 that operates in this case to hold the strain relief member 117, and to make a fluid seal at the junction of the end of the Y-connector 112 and the strain relief member. An O-ring 118 at the junction of the Y-connector member 112 and the shaft 50 of the catheter seals the catheter from fluid leakage and the Teflon™ sleeve 56 permits free movement of the ultrasound transmission member 16 within the shaft 50 of the catheter.

Figure 7:
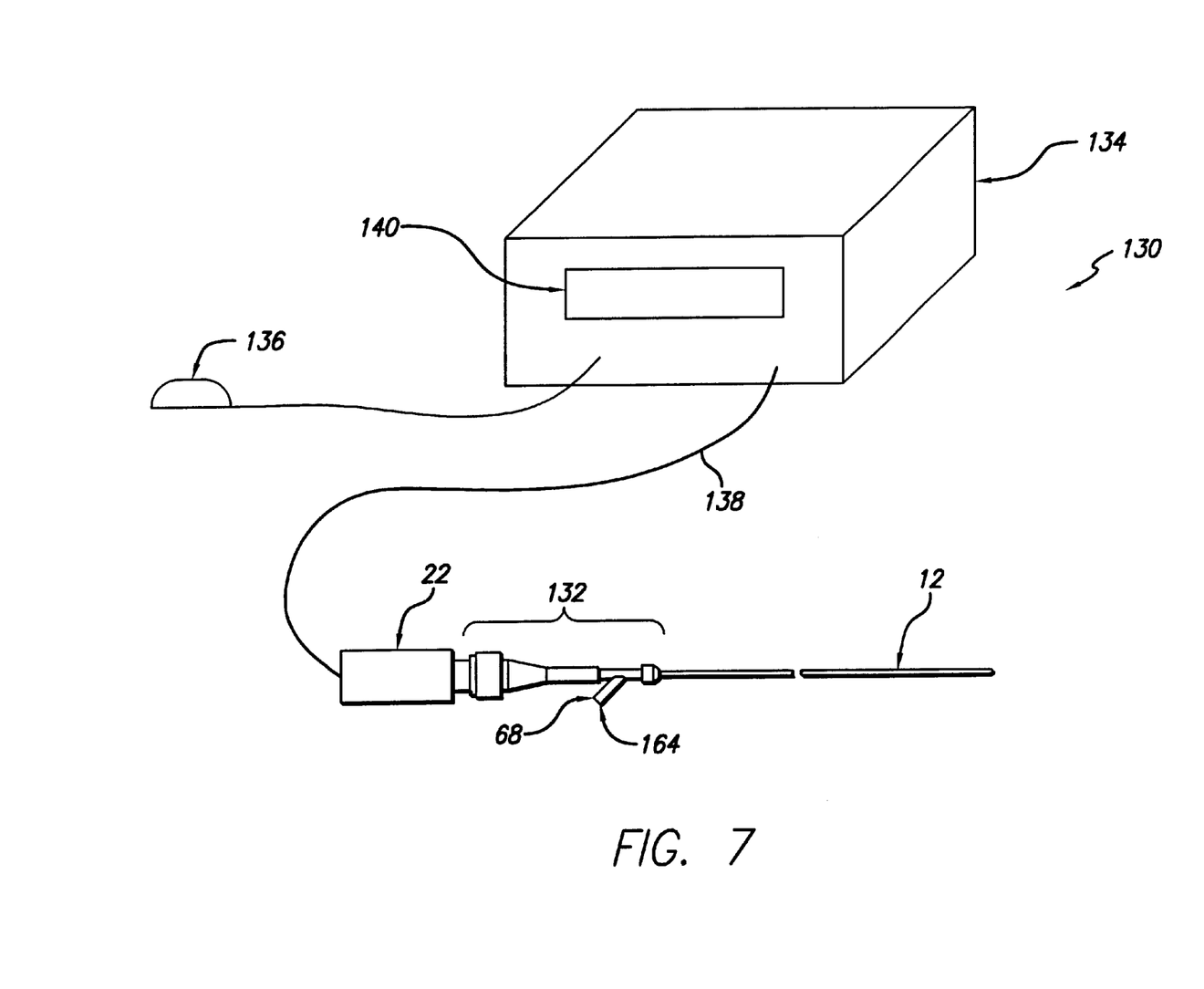
FIG. 7 is a general view of an ultrasonic energy delivery system in which a generator is connected to an ultrasonic transducer, which is connected to an ultrasonic angioplasty device. The generator is controlled by a foot switch.

The system view in FIG. 7 is of an over-the-wire ultrasound catheter system 130 in which a catheter 12 has a proximal end connector assembly 132 mounted on the proximal end thereof. As used herein, the term "over-the-wire" shall refer to a catheter that has a guide wire passage lumen formed within the body of the catheter such that a flexible guide wire may be advanced through the body of the catheter and out of a guide wire passage aperture formed in the distal end of the catheter. Returning to FIG. 7, an ultrasound transducer 22 is connected to the proximal end of the proximal connector assembly 132. An ultrasound generator 134 having a foot-actuated on/off switch 136 is operatively connected to the ultrasound transducer 22 through an electrical cable 138 so as to send ultrasonic energy through the ultrasound catheter 12, when desired. The generator 134 includes a display 140 that presents certain information about the ultrasonic energy application process.

The distal end of the catheter 12 may include a dilatation balloon, a stent, or other apparatus depending on the configuration selected and is configured to be percutaneously inserted into a body vascular system and through tortuous body lumina to a desired location within the body vascular system. The catheter 12 includes an ultrasound transmission wire (not shown) as described above.

Figure 8:
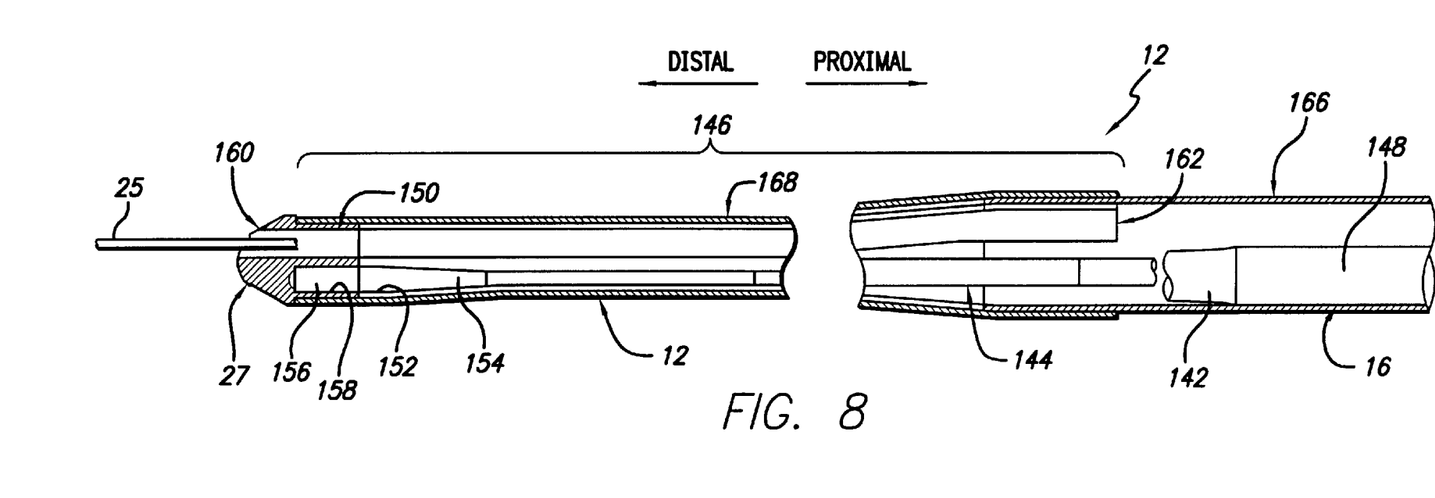
FIG. 8 is an enlarged view of the distal end of an ultrasonic angioplasty device showing the connection of an ultrasound transmission wire to a distal head, and showing a guide wire used in the catheter in an over-the-wire ("OTW") configuration and received in an aperture of the distal head.

Turning now to FIG. 8, a sectional view of part of the catheter 12 is shown. An ultrasound transmission member 16 includes tapering 142 for amplification at its distal end. The taper 142 terminates in a reduced diameter section 144 of the ultrasound transmission member 16. Because the reduced diameter distal portion 144 of the ultrasound transmission member 16 is of smaller cross-sectional diameter and less mass, it is more flexible and less rigid than the proximal portion thereof. In the embodiment of the catheter 12 shown in FIG. 8, the outer diameter of the distal portion 146 of the catheter is also reduced to coincide with the reduced diameter distal portion 144 of the ultrasonic transmission member 16, and also will exhibit less rigidity and greater flexibility than the remainder of the catheter body.

The present embodiment further includes an optional improvement to the ultrasound transmission member 16, said improvement comprising the disposition of a low friction coating or jacket 148 on the outer surface of all or a portion of the ultrasound transmission member 16. The low friction coating or jacket 148 may be disposed on the outer surface of the ultrasound transmission member so as to completely cover the ultrasound transmission member along its entire length, or along a discrete region or regions thereof. Such coating or jacket may comprise a layer of low friction polymer material such as polytetrafluoroethylene (ptfe) (Teflon™ Dupont, Inc., Wilmington, Del.) or other plastic materials such as polyethylene. The coating or jacket may be applied as a liquid and subsequently allowed to cure or harden on the surface of the ultrasound transmission member 16. Alternatively, the coating or jacket may be in the form of an elongate tube slidably disposable over the outer surface of the ultrasound transmission member. Such coating or jacket serves to prevent or diminish friction between the outer surface of the ultrasound transmission member 16 and the adjacent structures of the catheter or proximal end connector assembly 132 through which the ultrasound transmission member 16 extends.

A distal head 27 is firmly bonded, attached, or connected to the catheter body 12 such that the distal head is prevented from undergoing longitudinal or transverse movement separate from or relative to the catheter body. Additionally, such affixation of the distal head to the catheter body increases the conveyance of ultrasound energy into the distal portion of the catheter body 12, thereby resulting in enhanced cavitation effects created by the distal portion of the catheter body. Such bonding connection or attachment of the distal head 27 to the catheter body 12 may be accomplished by any suitable means. One means of attaching the distal head 27 to the catheter body 12 is through the use of an adhesive.

In the embodiment shown in FIG. 8, the adhesive is applied to the neck portion 150 of the distal head 27 prior to insertion thereof into the distal end of the lumen 152 of the catheter body 12. The adhesive may comprise any suitable adhesive, such as cyanoacrylate (e.g. Loctite™, Loctite Corp., Ontario, CANADA or Dron Alpha™, Borden, Inc., Columbus, Ohio) or polyurethane (e.g. Dymax™, Dymax Engineering Adhesive, Torrington, CN) to firmly bond and attach the distal head 27 to the catheter body 12.

The distal head 27 may be formed of any suitable rigid material such as metal or plastic. In devices wherein the distal head is formed of plastic, the surrounding plastic catheter body 12 may be thoroughly welded, heat sealed, or solvent welded to the plastic distal head 27, in accordance with the types of plastics employed.

In the alternative to the use of adhesives, various mechanical or frictional connectors, such as screw threads, lugs or other surface modifications formed on the neck portion 150 of the distal head 27, may be utilized to hold the distal head 27 in a fixed position relative to the catheter body 12. In such embodiments, corresponding grooves, detents or surface modifications may also be formed in the surrounding inner wall of the catheter body 12 so as to cooperate with any such threads, lugs or other surface modifications formed on the opposing surface of the distal head 27. Such threads, lugs or other surface modifications will be configured and constructed so as to mechanically or frictionally hold the distal head 27 in fixed position relative to the catheter body 12.

The distal head 27 is preferably formed of radio dense material so as to be easily discernable by radiographic means. Accordingly, the distal head 27 may preferably be formed of metal or, alternatively, may be formed of plastic, ceramic or rubber materials, optionally having one or more radio dense markers fixed thereto or formed therein. For example, the distal head 27 may be molded of plastic such as acrylonitrile-butadiene-styrene (ABS) and one or more metallic foil strips or other radio opaque markers may be affixed to such plastic distal head 27 in order to impart sufficient radio density to permit the distal head to be readily located by radiographic means. Additionally, in embodiments wherein the distal head is formed of molded plastic or other non-metallic material, a quantity of radio dense filler such as powdered bismuth or $BaSO_4$ may be disposed within the plastic or other non-metallic material of which the distal head is formed so as to impart enhanced radio density to the distal head.

The ultrasound transmission member 16 is tapered outward 154 at its most distal extreme 156 to a size that fits within a cavity 158 formed in the distal head 27. Although this outward taper attenuates the ultrasonic energy somewhat, it results in greater stability of the ultrasound transmission member 16 at the distal end because there is more surface area provided for adhesive attachment to the distal head and less likelihood of breakage at the attachment point.

Also shown in FIG. 8 is a guide wire 25 disposed in a guide wire aperture 160 formed in the distal head 27. The catheter body may include a separate guide wire lumen 162 within which the guide wire is disposed thus forming an over-the-wire (OTW) catheter arrangement. The guide wire may be introduced and retracted from the catheter body through a side arm 164 having a guide wire port 68 shown in FIG. 7.

Another feature of the catheter 12 is shown in FIG. 8. At the distal end 146, two tubular members are joined to result in the catheter shaft. In particular, a first tubular member 166 is used for the proximal and center sections of the catheter shaft while a second tubular member 168 is used for the distal section 146. As shown, the second, distal, tubular member 168 overlaps the first tubular member. The two members may be held together with adhesive. Such configuration to the catheter enables more cost effective manufacturing techniques as well as greater accuracy in manufacturing the catheter.

Figure 9:
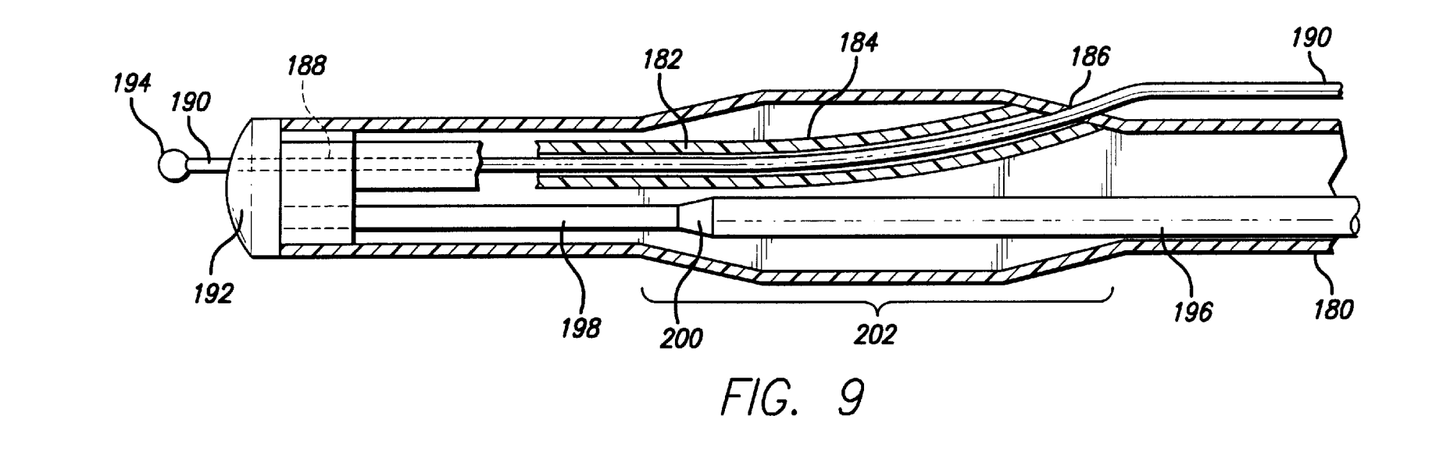
FIG. 9 is a diagram of a rapid exchange ("RX") catheter using the ultrasound transmission guide wire of FIG. 1, and showing various details of the ultrasound catheter distal end.

Turning now to FIG. 9, a rapid exchange or "RX" embodiment of a catheter is shown. In this embodiment, the catheter body 180 may be provided with a distal guide wire passage tube 182 positioned within the inner bore or lumen 184 of the catheter body 180 and extending from a guide wire re-entry aperture 186 to the guide wire passage aperture 188 formed in the distal head 192 of the device. As such, the proximal end member (not shown) of a guide wire 190 may be inserted into the distal head 192 of the catheter body 180 through the guide wire passage aperture 188 and subsequently disposed in a proximal direction through the guide wire lumen 184 of the guide wire tube 182 to a point where the proximal end of the guide wire 190 emerges from the guide wire entry/re-entry aperture 186. After emerging from the guide were entry/re-entry aperture 186, the proximal portion (not shown) of the guide wire 190 may extend and/or reside adjacent the outer surface of the proximal portion (not shown) of the catheter body 180. The catheter body 180 and the guide wire 190 may then be distally and/or proximally repositioned, relative to one another, during the procedure. Also, if desired, the guide wire 190 may be fully withdrawn and extracted by pulling the guide wire in a proximal direction such that the distal tip 194 of the guide wire is pulled through the distal head 192, through the guide wire passage tube 182, and out of the guide wire entry/reentry aperture 186, and the guide wire 190 is subsequently fully withdrawn from the catheter body 180, leaving only the ultrasound catheter in place in the patient.

The distal portion of the catheter shown in FIG. 9 contains many of the same elements shown in other figures. In particular, the distal head 192 is fixedly attached to the catheter body 180 through adhesive or other means. An ultrasound transmission wire 196 is attached to the distal head 192 and has a stepped down length 198 with a conical transition area 200. An enlarged area 202 of the distal portion is used to accommodate the additional guide wire tube 182 in this RX embodiment.

Although embodiments shown and described herein include OTW and RX catheters, other embodiments are possible that include combinations or hybrids of OTW and RX. As is apparent, an RX catheter system is easily used with the ultrasound transmission guide wire described and shown.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An ultrasonic angioplasty device for connection to an ultrasound transducer, the ultrasonic angioplasty device comprising:

an elongated catheter body having a lumen extending longitudinally therethrough, the catheter body having a proximal end and a distal end;

an ultrasound transmission member located in the lumen of the catheter body and having a distal end for applying ultrasonic energy to a biological subject, and having a proximal end;

a connector assembly configured to connect the proximal end of the ultrasound transmission member to an ultrasound transducer and having a surface defining a transverse bore extending at least partially through the connector assembly; and a rotation control device comprising a control shaft disposed at the proximal end of the ultrasound transmission member and coupled to the proximal end of the elongated catheter body such that rotation of the control shaft controls rotation of the catheter body, the control shaft having a surface defining a transverse bore extending at least partially through the control shaft, and the rotation control device further comprising a dowel member disposed in the transverse bores of the control shaft and the connector assembly to align the control shaft and the connector assembly to prevent rotation of the connector assembly and the ultrasound transmission member relative to the control shaft thereby preventing rotation of the ultrasound transmission member relative to the catheter body.

2. The ultrasonic angioplasty device of claim 1 wherein the connector assembly comprises:

a compressible gripping ferrule having a surface defining an aperture through which the ultrasound transmission member passes;

a front connector screw member having a surface defining an aperture through which the ultrasound transmission member passes and having an exterior threaded portion; and a crimp screw connector member connectable to the ultrasound transducer, the crimp screw connector member having a surface defining an aperture through which the ultrasound transmission member passes and having a longitudinal bore in which the compressible gripping ferrule is disposed, the longitudinal bore having an internally threaded portion for threadedly receiving the exterior threaded portion of the front connector screw member, whereby the front connector screw member compresses the gripping ferrule in the crimp screw connector member, to cause the gripping ferrule to firmly grip and hold the ultrasound transmission member;

wherein the transverse bore of the connector assembly is located in the crimp screw connector member.

3. An ultrasonic angioplasty device for connection to an ultrasound transducer for applying ultrasonic energy to a lesion, the angioplasty device comprising:

an elongated catheter body having a lumen extending longitudinally therethrough, the catheter body having a distal and a proximal end;

an ultrasound transmission member extending through the catheter body, the ultrasound transmission member having a distal head located at the distal end of the catheter body for applying ultrasonic energy to a lesion, and having a proximal end;

a connector assembly connected to the proximal end of the ultrasound transmission member and configured to connect to an ultrasound transducer, the connector assembly having multiple surfaces each defining a transverse bore extending at least partially through the connector assembly; and a rotation control device comprising a control shaft disposed at the proximal end of the ultrasound transmission member and coupled to the proximal end of the elongated catheter body such that rotation of the control shaft controls rotation of the catheter body, the control shaft having multiple surfaces each defining a transverse bore extending at least partially through the control shaft, and the rotation control device further comprising multiple dowels, each dowel being disposed in the transverse bores of the control shaft and the connector assembly to align the control shaft and the connector assembly to prevent rotation of the connector assembly and the ultrasound transmission member relative to the control shaft thereby preventing rotation of the ultrasound transmission member relative to the catheter body.

4. The ultrasonic angioplasty device of claim 3 wherein the connector assembly comprises:

a compressible gripping ferrule having a surface defining an aperture through which the ultrasound transmission member passes;

a front connector screw member having a surface defining an aperture through which the ultrasound transmission member passes and having an exterior threaded portion; and a crimp screw connector member connectable to the ultrasound transducer, the crimp screw connector member having a surface defining an aperture through which the ultrasound transmission member passes and having a longitudinal bore in which the compressible gripping ferrule is disposed, the longitudinal bore having an internally threaded portion for threadedly receiving the exterior threaded portion of the front connector screw member, whereby the front connector screw member compresses the gripping ferrule in the crimp screw connector member, to cause the gripping ferrule to firmly grip and hold the ultrasound transmission member;

wherein the transverse bores of the connector assembly are located in the crimp screw connector member.

5. The ultrasonic angioplasty device of claim 4 wherein the transverse bores of both the control shaft and crimp screw connector member are disposed at angles of 120 degrees from each other.

6. An ultrasonic angioplasty device, comprising:

an elongated catheter body having a lumen extending longitudinally therethrough;

an ultrasound transmission member disposed in the lumen of the elongated catheter body, the ultrasound transmission member having a distal end for applying ultrasonic energy to an area of vascular blockage and a proximal end;

a guide wire passage disposed within the elongated catheter body for receiving a guide wire;

a single-piece connector member connected directly to the proximal end of the ultrasound transmission member and configured to connect directly to an ultrasound transducer, the single-piece connector member having a surface defining a transverse bore extending at least partially through the connector member; and a rotation control device comprising a control shaft disposed at the proximal end of the ultrasound transmission member and coupled to the proximal end of the elongated catheter body such that rotation of the control shaft controls rotation of the catheter body, the control shaft having a surface defining a transverse bore extending at least partially through the control shaft, and the rotation control device further comprising a dowel member disposed in the transverse bores of the control shaft and the connector member to align the control shaft and the connector member to prevent rotation of the connector member and the ultrasound transmission member relative to the control shaft thereby preventing rotation of the ultrasound transmission member relative to the catheter body.

7. The ultrasonic angioplasty device of claim 6 further comprising a distal head attached to the distal end of the catheter and attached to the distal end of the ultrasound transmission wire for applying ultrasonic energy to a lesion, the distal head having a guide wire aperture through which a guide wire may be extended and retracted.

8. The ultrasonic angioplasty device of claim 6 wherein the connector member has a proximal end having an exterior threaded portion for threadedly engaging an internally threaded portion of the ultrasound transducer.

9. The ultrasonic angioplasty device of claim 6 wherein the connector member has multiple surfaces each defining a transverse bore extending at least partially through the connector member, the control shaft has multiple surfaces each defining a transverse bore extending at least partially through the control shaft, and the rotation control device comprises multiple dowel members, each dowel member being disposed in the transverse bores of the control shaft and the connector member.

10. The ultrasonic angioplasty device of claim 6 wherein the connector member has a distal end having a surface defining an aperture through which the ultrasound transmission member passes, the connector member being crimped around the ultrasound transmission member to secure it in place.

11. The ultrasonic angioplasty device of claim 10 wherein the connector member has a distal end having a surface defining an aperture through which the ultrasound transmission member passes and a proximal end, the ultrasound transmission member extending through the connector member to the proximal end and the proximal end of the connector member being crimped around the ultrasound transmission member to secure it in place.

12. The ultrasonic angioplasty device of claim 11 wherein the transverse bores of both the control shaft and connector member are disposed at angles of 120 degrees from each other.

* * * * *